US009192390B2

(12) United States Patent
delRio et al.

(10) Patent No.: US 9,192,390 B2
(45) Date of Patent: Nov. 24, 2015

(54) SURGICAL SAW BLADE (71) Applicant: Synthes USA, LLC, West Chester, PA (US)

(72) Inventors: Eddy H. delRio, Palm Beach Gardens, FL (US); David Narducci, Lake Worth, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 353 days.

(21) Appl. No.: 13/715,219

(22) Filed: Dec. 14, 2012

(65) Prior Publication Data
US 2014/0171950 A1 Jun. 19, 2014

(51) Int. Cl.
A61B 17/14 (2006.01)
A61B 17/32 (2006.01)
B23B 31/12 (2006.01)
B23B 31/18 (2006.01)
B23B 31/19 (2006.01)
B23D 35/00 (2006.01)
B23D 59/00 (2006.01)
B27B 19/00 (2006.01)

(52) U.S. Cl.
CPC .............. *A61B 17/148* (2013.01); *A61B 17/14* (2013.01); *A61B 17/32* (2013.01); *A61B 17/32002* (2013.01); *B23B 31/1261* (2013.01); *B23B 31/18* (2013.01); *B23B 31/185* (2013.01); *B23B 31/19* (2013.01); *B23D 35/002* (2013.01); *B23D 35/005* (2013.01); *B23D 59/002* (2013.01); *B27B 19/006* (2013.01); *A61B 17/141* (2013.01); *A61B 2017/320028* (2013.01)

(58) Field of Classification Search
CPC .... A61B 17/14; A61B 17/141; A61B 17/148; A61B 17/32; A61B 17/32002; A61B 2017/320028; B23B 31/1261; B23B 31/18; B23B 31/185; B23B 31/19; B23D 35/002; B23D 35/005; B23D 59/002; B27B 19/006
See application file for complete search history.

(56) References Cited

U.S. PATENT DOCUMENTS

| 4,386,609 | A  | * | 6/1983  | Mongeon ........................ 606/53 |
| 5,263,972 | A  | * | 11/1993 | Evans et al. .................... 606/176 |
| 5,382,249 | A  |   | 1/1995  | Fletcher |
| 5,729,904 | A  | * | 3/1998  | Trott ............................... 30/339 |
| 7,833,241 | B2 | * | 11/2010 | Gant ............................. 606/176 |
| 7,833,244 | B2 |   | 11/2010 | Cerundolo |
| 2002/0198556 | A1 | * | 12/2002 | Ark et al. ...................... 606/178 |
| 2012/0292864 | A1 | * | 11/2012 | Zhou ............................. 279/141 |

FOREIGN PATENT DOCUMENTS

EP 0776634 6/1997
WO 2004/043269 5/2004

OTHER PUBLICATIONS

European Search Report, dated Feb. 17, 2014, received in connection with corresponding European Application No. 13197145.9.
Partial European Search Report, dated Feb. 17, 2014, received in connection with corresponding European Application No. 13197145.9.

* cited by examiner

*Primary Examiner* — Larry E Waggle, Jr.
(74) *Attorney, Agent, or Firm* — Meunier Carlin & Curfman LLC (57) ABSTRACT

The present invention is directed to a surgical cutting device configured to drive a removable surgical saw blade in oscillating rotation. The saw blade is held within the cutting device at a holding member and a clamping member and removeabley attached to a drive plate.

20 Claims, 4 Drawing Sheets

FIG. 13

SURGICAL SAW BLADE

TECHNICAL FIELD

This invention relates generally to powered surgical cutting devices and, more particularly, to devices including a saw blade driven through rotational oscillations.

BACKGROUND

During a surgical procedure, a surgeon may use a motorized saw for cutting bone and other tissue. Such systems generally include a replaceable blade mounted to a drive mechanism. To prevent trauma to the patient and in an attempt to reduce damage to surrounding tissue, the surgeon orients the saw blade within the patient at particular angle during the cutting operation. Current systems do not provide saw blades that are fixed to the drive mechanism and to not provide for efficient orientation of the blade within the patient. Therefore, a need in the art exists for a device that provides for the orientation of the saw blade with respect to the drive mechanism that is both efficient and reduces patient trauma.

SUMMARY

Presented are systems and methods for a surgical cutting device including a saw blade driven through rotational oscillations. An aspect of the present disclosure is directed to a surgical saw apparatus including a holding member, a clamping member and a releasing pin. The holding member may include an outer surface and an elongated slot open at a first end, wherein the elongated slot includes spaced apart elongated sides, a holding surface extending between the elongated sides, and an end surface at a second end, opposite the first end of the slot. The clamping member may include a clamping surface disposed adjacent the elongated slot and movable within the elongated slot. The releasing pin may include a first end, rigidly attached to the clamping member and slidably attached to the holding member, a second end disposed away from the clamping member and the holding member, and an axis extending between the first and second ends. Moving the releasing pin relative to the holding member, in a releasing direction, parallel to the axis of the releasing pin, may move the clamping surface away from the holding surface.

Another aspect of the present disclosure is directed to a surgical saw apparatus including a housing, a drive plate, a holding member, a clamping member and a releasing pin. The holding member may be mounted to rotate about an axis of rotation, where the holding member may be held within an engaged position to rotate with the drive plate. The holding member may additionally be movable into a released position to rotate independently from the drive plate. The clamping member may be mounted to rotate with the holding member about the axis of rotation and may also be held on the holding member in a clamping position. The clamping member may be movable away from the holding member into an open position, wherein the holding member and the clamping member in the clamping position form an elongated slot, having an open end, for holding a shank of a surgical saw blade having a blade portion extending outward from the open end of the elongated slot. The holding member and the clamping member in the clamping position may form an elongated slot for releasing the shank of a surgical saw blade for removal through the open end of the elongated slot. The releasing pin may hold the holding member in the engaged position while additionally holding the clamping member in the engaged position. The releasing pin may be movable into a released position, wherein the releasing pin in the releasing position holds the holding member in the released position and the clamping member in the open position.

A further aspect of the present disclosure is directed to a surgical saw apparatus including a surgical saw blade, a housing, a drive plate and a holding member. The drive plate may be mounted in the housing to rotate about an axis of rotation and driven in oscillating rotation. The drive play may have a groove radially displaced from the axis of rotation. The holding member may be releasably hold the surgical saw blade. The holding member may include a tooth extending toward the drive plate. The holding member may be mounted in the housing to rotate about an axis of rotation and may slide along the axis of rotation in a releasing direction from an engaged position, in which the tooth is held within the groove to a released portion, in which the tooth is held away from the groove, and opposite the releasing direction.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

DETAILED DESCRIPTION

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components may be described herein as extending horizontally along a longitudinal direction and lateral direction, and vertically along a transverse direction. Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting.

Figure 1:
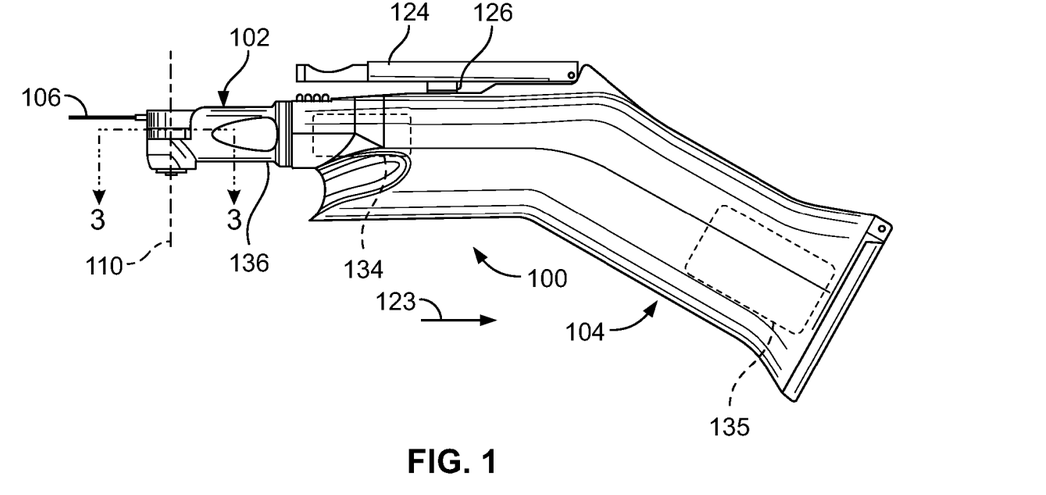
FIG. 1 is a right side elevation of a surgical cutting device built in accordance with the invention.
Figure 2:
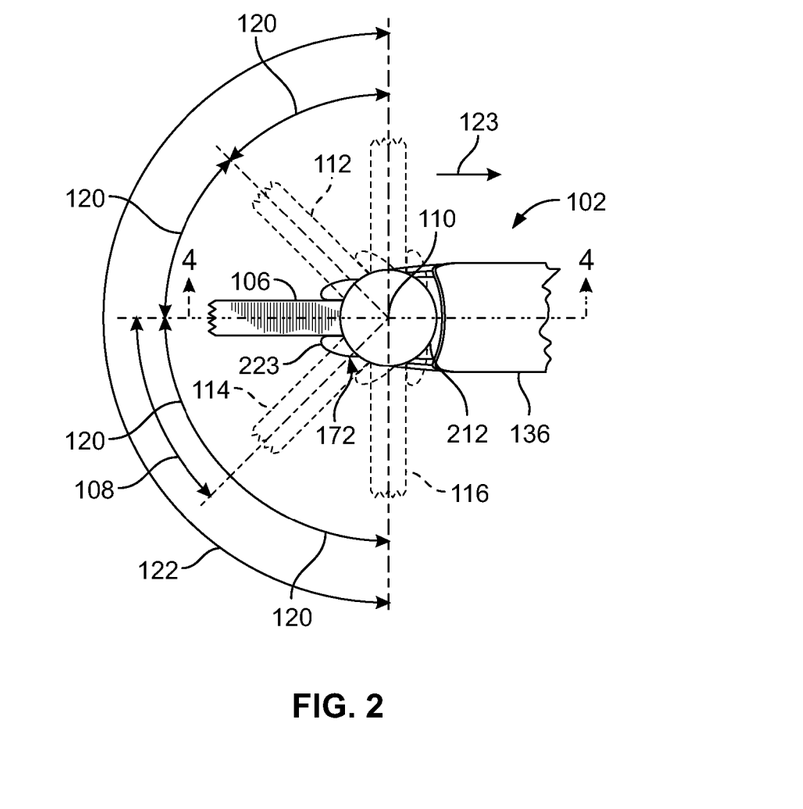
FIG. 2 is a plan view of a drive head within the surgical cutting device of FIG. 1.

Certain examples of the invention will now be described with reference to the drawings. In general, such embodiments relate to a surgical cutting device 100 including a saw blade driven through rotational oscillations. External features of an example surgical cutting device 100 will first be discussed in reference to FIGS. 1 and 2. FIG. 1 is a right-side elevation of an example surgical cutting device 100 and FIG. 2 is a plan view of an example drive head 102 associated with the surgical cutting device 100.

The surgical cutting device 100 includes the drive head 102 and a handle portion 104. A surgical saw blade 106 is held and rotatably driven in oscillation through an angle 108 about an axis of rotation 110. The angle 108 can include any portion of the radius defined by the rotation surgical saw blade 106 around axis 110. For example, the angle 108 can be equal to a 45-degree segment such that the surgical saw blade 106 is driven through a 45-degree angle between the position shown in FIG. 2 in solid lines and a position indicated by dashed lines 112. Alternately, the drive mechanism 130 within the drive head 102 can be configured to oscillate the surgical saw blade 106 in 45-degree increments so that the surgical saw blade 106 is driven, for example, between the positions indicated by dashed lines 114 and the position indicated by dashed lines 116.

The angle 108 can include semi-circle 122 formed around the axis 110. The angle 108 and/or the semi-circle 122 can be divided into segments. The segments can include any portion of the angle 108 defined by the rotation surgical saw blade 106 around axis 110. For example, as illustrated in FIG. 2, the semi-circle 122 can include four corresponding 45-degree segments 120. The drive head 102 can be configured to drive the surgical saw blade 106 through each of the four segments 120 around the axis of rotation 110. In a further example, the angle 108 and/or semi-circle 122 can include any number of segments 120 around axis 110 and the drive head 102 can be configured to drive the surgical saw blade 106 through each of the segments 120. In another example, the drive head 102 can be configured to drive the surgical saw blade 106 continuously through the entire angle 108 and/or semi-circle 122 defined by the rotation surgical saw blade 106 around axis 110. In a further example (not shown), the drive head 102 can be configured to drive the surgical saw blade through any angle defined by the 360-degree rotation of the surgical saw blade 106 around axis 110.

As illustrated in FIG. 1, the handle portion 104 may extend outward from axis 110 in the direction of arrow 123. An example handle portion 104 extends perpendicular to the axis 110. As a result, each of the segments 120 may have a different angular relationship about the axis 110 with respect to the handle portion 104. The ability to configure the drive head 102 so that the surgical saw blade 106 operates within any one of the segments 120 can be used to facilitate reaching different areas within a patient using the surgical saw blade 106 while holding the handle portion 104 at a fixed location. The handle portion 104 may also include a control lever 124 in contact with an electrical switch 126 configured to control operation of the drive mechanism 130. For example, the switch 126 can be used to turn the drive mechanism 130 on and off. The control lever 124 can be used, for example, to control the drive speed of the saw blade 106.

Figure 3:
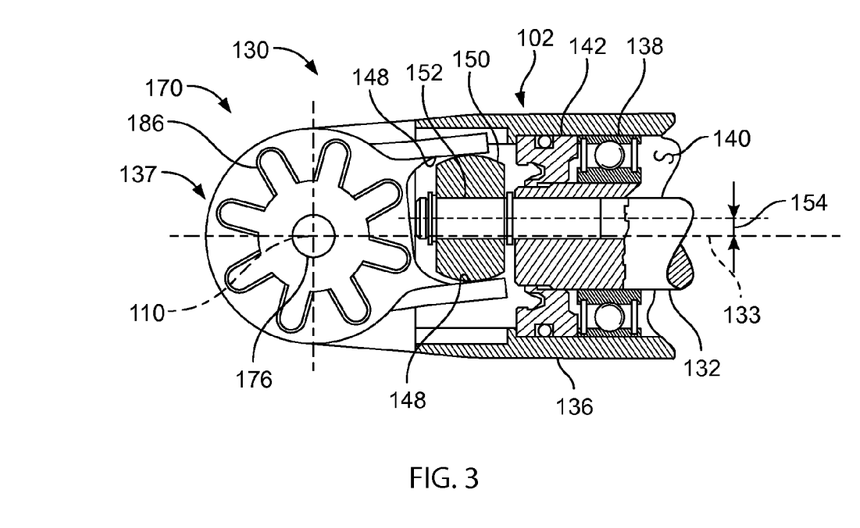
FIG. 3 is a cross-sectional plan view of the drive head of FIG. 2, taken as indicated by section lines 3-3 in FIG. 1.
Figure 4:
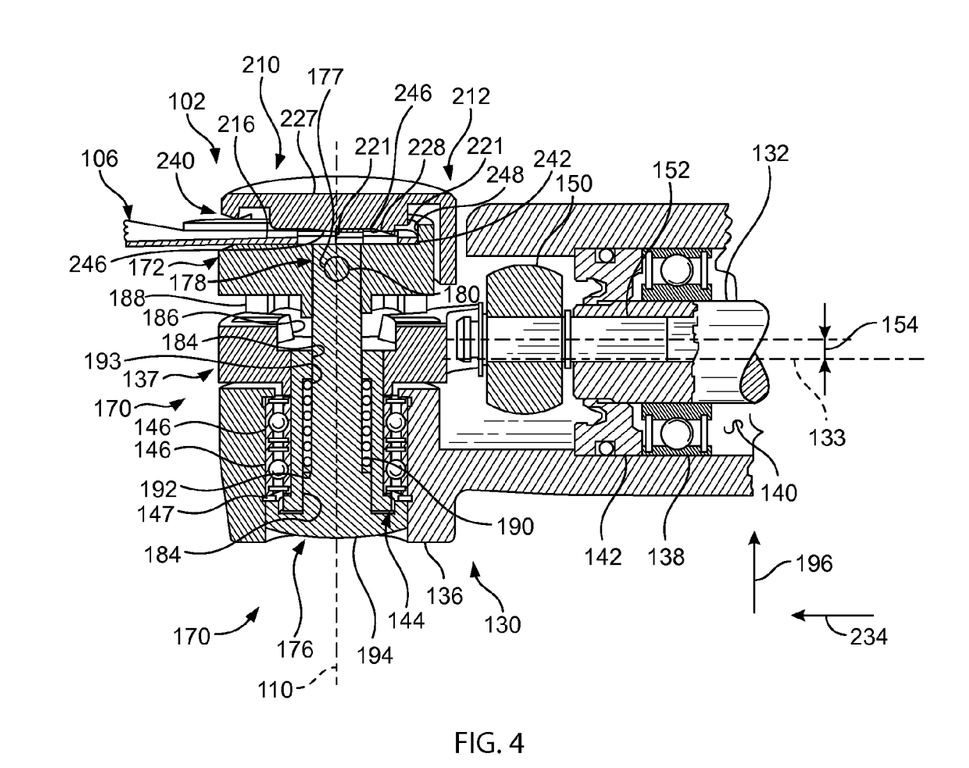
FIG. 4 is a first cross-sectional right side elevation of the drive head of FIG. 2, taken as indicated by section lines 4-4 therein to show a blade holding mechanism therein in an open position with a locking mechanism therein in a released position.

The drive mechanism 130 used for producing oscillating rotation of the surgical saw blade 106 about the axis 110 will now be discussed in reference to FIGS. 3 and 4. FIG. 3 is a cross-sectional plan view of the drive head 102 within the surgical cutting device 100, taken as indicated by section lines 3-3 in FIG. 1. FIG. 4 is a cross-sectional right side elevation of the drive head 102, taken as indicated by section lines 4-4 in FIG. 2.

Within the drive mechanism 130, the continuous rotation of a drive shaft 132 about a drive axis 133 is converted into an oscillating rotation of a drive plate 137 about the axis of rotation 110, which is perpendicular to the drive axis 133. The drive shaft 132 is driven by a power source. An example power source can include an electric motor 134 (shown in FIG. 1) extending into the handle portion 104 from the drive head 102, with power being provided by a battery pack 135, also within the handle portion 104. The drive shaft 132 is rotatably mounted within a housing 136 of the drive head 102. For example, the drive shaft 132 may be mounted using a ball bearing 138. Contamination between the distal end of the drive mechanism 130 and the space 140 within the housing 136 is prevented by a seal 142. The seal 142 can include a spring loaded lip and an o-ring to maintain contact with the housing 136. The drive plate 137 includes a sleeve 144, which is mounted to rotate within the housing 136 about the axis 110 by a pair of ball bearings 146, which are held in place by a retaining clip 147. The drive plate 137 includes a pair of spaced-apart contact surfaces 148, between which a roller 150 is disposed, with the roller 150 being rotatably mounted on an eccentric shaft 152, which is in turn attached to the drive shaft 132 at a radial distance 154 from the drive axis 133, so that the drive plate 137 oscillates in rotation as the drive shaft 132 is driven. The drive shaft 132 can be driven at variable rotational speed. For example, the rotational speed of the drive shaft 132 can be varied based on the angle of the control lever 124.

Figure 5:
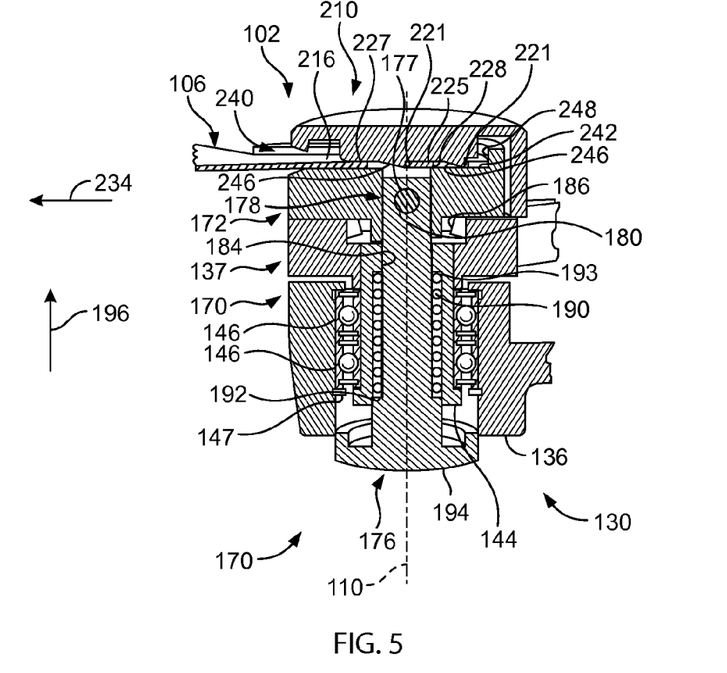
FIG. 5 is a second cross-sectional right side elevation of the drive head of FIG. 2, additionally taken as indicated by section lines 4-4 to show the blade holding mechanism in a clamping position with the locking mechanism therein in an engaged position.
Figure 6:
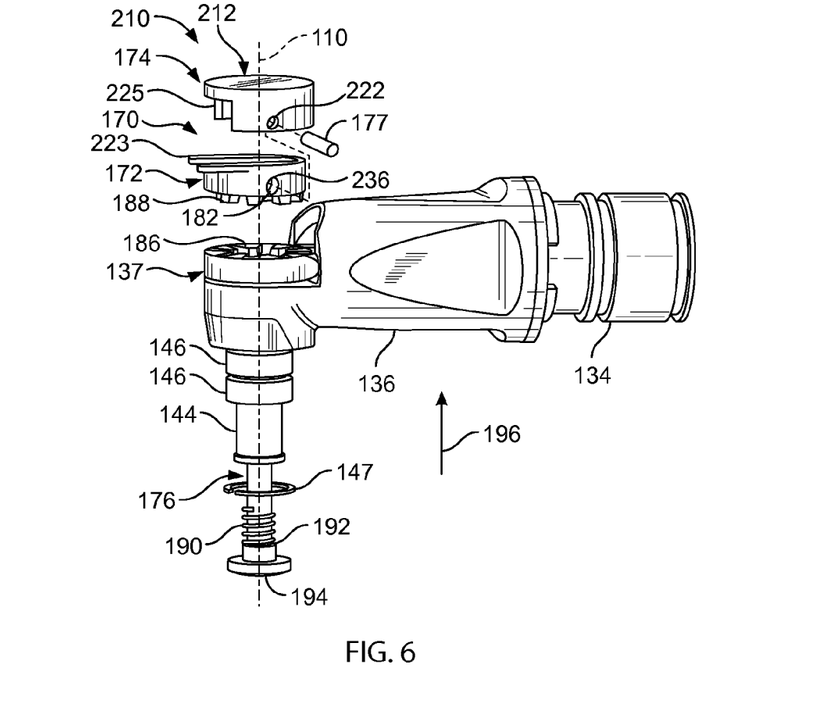
FIG. 6 is a perspective view of the drive head of FIG. 2, showing elements therein in an exploded relationship with one another.

A locking mechanism 170 for engaging a holding member 172 to the drive plate 137 at various positions to determine the particular angle and/or segment 120 through which the saw blade 106 will be driven, as discussed above in reference to FIG. 2, will now be discussed, with continued reference being made to FIGS. 3 and 4, and with additional reference being made to FIGS. 5 and 6. FIG. 5 is a cross-sectional elevation of the drive head 102, which is similar to FIG. 4, except that, in FIG. 4, a saw blade holding mechanism 174 is shown in an open position, allowing the insertion of a surgical saw blade 106 therein, or its removal therefrom. FIG. 6 is a perspective view of the drive head 102, showing elements therein in an exploded relationship with one another.

The holding member 172 is slidably and rotatably attached to the drive plate 137 by means of a releasing pin 176, with a sliding connection between the holding member 172 and the releasing pin 176 being formed by a cross pin 177 extending from a first end 178 of the releasing pin 176 through holes 180 in the releasing pin 176 and through slots 182 in the holding member 172. A sliding and rotating connection is made between the releasing pin 176 and a central hole 184 extending through the sleeve 144. The drive plate 137 includes a plurality of grooves 186 arranged in a circular pattern about the axis 110, while the holding member 172 includes a plurality of teeth 188, which are arranged in another circular pattern and configured to engage the grooves 186 when the drive plate 137 and the holding member 172 are held together, as shown in FIG. 5. In another example, when the drive plate 137 and the holding member 172 are held apart, as shown in FIG. 4, the teeth 188 are held out of engagement with the grooves 186, allowing the holding member to be rotated about the axis 110.

The locking mechanism 170 is held in the engaged position of FIG. 5, with the holding member 172 engaging the drive plate 137 by a compression spring 190 pushing against an outward extending flange 192, facing in the releasing direction of arrow 196, forming a portion of the releasing pin 176. The compression spring 190 is held between a flange 192 and an inward-extending flange 193 within the central hole 184 of the sleeve 144. The locking mechanism 170 is moved into the released position of FIG. 4 when the user pushes a button surface, formed at a second end 194 of the releasing pin 176, in the releasing direction of arrow 196. With the locking mechanism 170 in the released position, the user can rotate the holding member 172 about the axis 110 to determine the angle and/or segment 120 (shown in FIG. 2) through which the surgical saw blade 106 is driven. When the second end 194 is then released, the compression spring 190 pushes the holding member 172 into engagement with the drive plate 137.

The grooves 186 and the teeth 188 may be tapered to minimize an amount of rotational wiggling of the holding member 172 needed to begin the process of engaging the holding member 172 with the drive plate 137.

Figure 7:
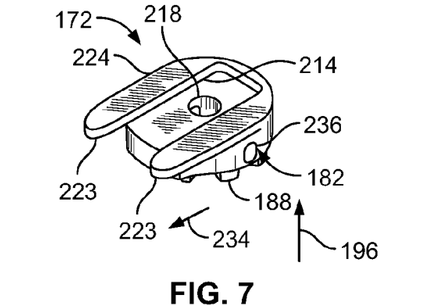
FIG. 7 is a perspective view of a holding member within the drive head of FIG. 2, shown as viewed from above.
Figure 8:
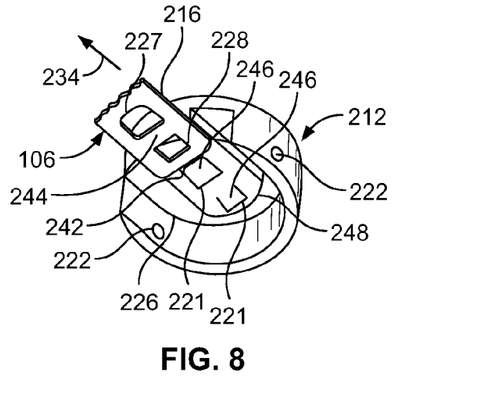
FIG. 8 is a perspective view of a clamping member within the drive head of FIG. 2, shown as viewed from below.

A saw blade holding mechanism 210 will now be discussed, with continued reference being made to FIGS. 4-6, and with additional reference being made to FIGS. 7 and 8. FIG. 7 is a perspective view of the holding member 172, as viewed from below and FIG. 8 is a perspective view of a clamping member 212, shown as viewed from below. The holding member 172 includes an elongated slot 214 for holding an elongated shank 216 of the saw blade 106, a central hole 218, into which the releasing pin 176 extends, and the transverse slot 182, which is elongated in the releasing direction of arrow 196, through which the cross pin 177 extends. The rigid attachment of the elongated shank 216 is supported by a pair of tabs 223 extending outward as parts of the holding member 172.

The clamping member 212 includes a pair of holes 222, into which the cross pin 177 is pressed and a pair of tapered lugs 221 for engaging and holding the elongated shank 216 of the saw blade 106 within apertures 227, 228 thereof. In this way, the clamping member 212 and the releasing pin 176 are held to one another to move together, while the holding member 172 can move along the releasing pin 176 through a distance permitted by the elongation of slot 182 therein.

When the saw blade holding mechanism 210 is assembled as shown in FIGS. 4 and 5, an upper portion 224 of the holding member 172 is disposed within a cavity 226 in the clamping member 212, with the tabs 223 extending outward, in the direction of arrow 234, through a slot 225 in the clamping member 212. The saw blade holding mechanism 210 is then held in the clamping position of FIG. 5 by the compression spring 190, which additionally holds the holding member 172 in engagement with the drive plate 137. For example, the compression spring 190 applies a force acting opposite the releasing direction of arrow 196 to a flange 192 of the releasing pin 176, with this force being transmitted through the releasing pin 176, the cross pin 177, and the clamping member 212 to apply a force to the elongated shank 216 of the surgical saw blade 106.

To remove the saw blade 106 from the saw blade holding mechanism 210, the user pushes the second end 194 at the end of the releasing pin 176 in the releasing direction of arrow 196, moving the clamping member 212 into the open position shown in FIG. 4. Since the clamping member 212 is attached to the releasing pin 176 by the cross pin 177 extending through round holes 222, the clamping member 212 moves with the releasing pin 176 as the user pushes on the second end 194. In another example, since the holding member 172 is attached to the releasing pin 176 by the cross pin 177 extending through the slotted holes 182, the holding member 172 may move with the clamping member 212 during its entire movement in the releasing direction of arrow 196. Otherwise, the holding member 172 may remain engaged with the drive plate 137 during a first part of the movement of the clamping member 212 in the releasing direction of arrow 196, with the holding member 172 then beginning to move in the releasing direction of arrow 196 when the moving cross pin 177 contacts an end 236 of the each slotted hole 182. In either case, the holding member 172 is moved completely out of engagement with the drive plate 137, with the teeth 188 being held apart from the grooves 186. Then, while retaining pressure on the second end 194 of the releasing pin 176 to hold the clamping member 212 in the open position of FIG. 4, the user moves the saw blade 106 opposite the releasing direction of arrow 196 so that the apertures 227, 228 within the saw blade shank 216 are moved away from the lugs 221 within the clamping member 212, allowing the saw blade 106 to be then removed by being pulled outward in the direction of arrow 234.

To insert the surgical saw blade 106 within the saw blade holding mechanism 210, the user again pushes the second end 194 of the releasing pin 176 in the releasing direction of arrow 196. For example, the saw blade holding mechanism 210 is constructed so that, even when the clamping member 212 and the holding member 172 270 are held together, a slot opening 240 remains, allowing the insertion of the elongated shank 216 to begin the insertion of the saw blade 106. As the saw blade 106 is then moved inward, opposite the direction of arrow 234, a proximal end 242 of the elongated shank 216 and a strap 244 between the apertures 227, 228 within the elongated shank 216 move along the slanted surfaces 246 of the lugs 221, the elongated shank 216 is pushed 275 opposite the releasing direction of arrow 196 by contact with these slanted surfaces 246, moving the holding member 172 out of the way if necessary. The elongated shank 216 is then been moved inward, opposite the direction of arrow 234 as far as possible, with the proximal end 242 being moved against an internal surface 248 of the clamping member 212, with the apertures 226, 227 then being aligned with the lugs 221. When the 280 user then releases pressure on the second end 194 of the releasing pin 176, the compression spring 190 moves the clamping member 212 and the holding member 172 opposite the releasing direction of arrow 196, with the elongated shank 216 is clamped between the clamping member 212 and the holding member 172, and the lugs 221 are held within the apertures 227, 228. This movement of the holding member 172 opposite 285 the releasing direction of arrow 196 engages the teeth 188 in the holding member 172 into the grooves 186 within the drive plate 137. It may be necessary for the user to wiggle the holding member 172 in rotation about the axis 110 to achieve proper engagement. Rotation of the holding member 172 about the axis 110 may be used to determine which of the angles and/or segments 120 (shown in FIG. 2) defines the angle 290 through which the saw blade 106 will be driven.

Figure 9:
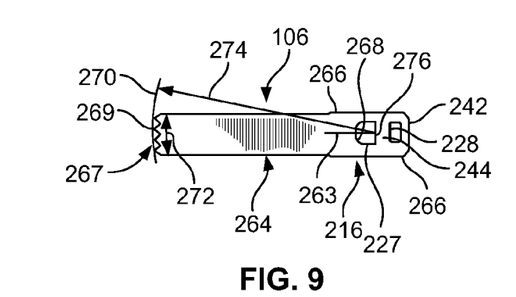
FIG. 9 is a plan view of a surgical saw blade within the surgical cutting device of FIG. 1.
Figure 10:
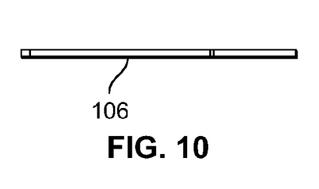
FIG. 10 is a side elevation of the surgical saw blade of FIG. 9.
Figure 11:
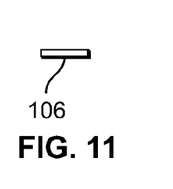
FIG. 11 is an end elevation of the surgical saw blade of FIG. 9.
Figure 12:
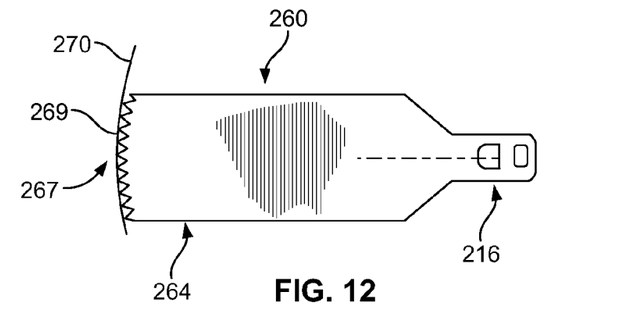
FIG. 12 is a first alternative surgical saw blade for use in the surgical cutting device of FIG. 1.
Figure 13:
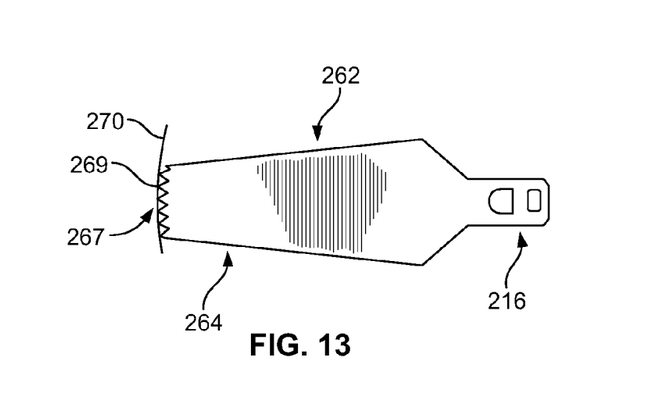
FIG. 13 is a second alternative surgical saw blade for use in the surgical cutting device of FIG. 1.

Various characteristics of the surgical saw blade 106 and of alternative saw blades will now be explained, with reference being made to FIGS. 9-13. FIGS. 9-11 show the surgical saw blade 106. FIG. 9 is a plan view of an example surgical saw blade 106, FIG. 10 is a side elevation, and FIG. 11 is an end elevation. FIG. 12 is a plan view of another example saw blade 260. FIG. 13 is a plan view of a further example saw blade 262.

In accordance with the invention, each of the saw blades 106, 260, 262 include a blade portion 264 and an elongated shank 216, having a proximal end 242, straight elongated sides 266, a distal aperture 227 and a proximal aperture 228. These features are symmetrical about a straight line of symmetry 263. Preferably, the distal aperture 227 includes a convex curved surface 268 closest to the blade portion 264. The curvature of the convex curved surface 268 can reduce a level of concentration of flexural stresses occurring during operation of the surgical cutting device 100.

A plurality of surgical saw blades, such as the saw blades 106, 260, 262, may be provided for alternative use within the surgical cutting device 100. The differences among the saw blades 106, 260, 262 occur within their respective blade portions 264. The elongated shanks 216 of saw blades 106, 260, 262 may be identical, each configured to fit tightly within the saw blade holding mechanism 210 as described above. A distal end 267 of each of the blade portions 264 includes a plurality of saw teeth 269, arranged along an arc 270 having a length 272 disposed at a radius 274 about an arcuate axis 276 within the elongated shank 216. When the elongated shank 216 is inserted into the saw blade locking mechanism 170, the arcuate axis 276 is aligned with the rotation 110. For example, the saw blades 106, 260 and 262 differ from one another in having different arcuate lengths 272 and/or radii 274.

Using the surgical cutting device 100 the process of changing saw blades 106 during a surgical procedure is greatly simplified. With the surgical cutting device 100, the user need only insert the elongated shank 216 into the elongated slot 214. Moreover, the saw blades 106 are narrower than previous designs leading to less material use, lower processing time, and less storage, resulting, ultimately, in a cost savings to the user. While the foregoing description and drawings represent examples of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed examples are, therefore, to be considered in all respects as illustrative and not restrictive, the scope of the invention being indicated by the appended claims and not limited to the foregoing description.

In addition, the various examples disclosed herein may be adapted for use in virtually any interior body region where the formation and/or augmentation of a cavity within tissue is required for a therapeutic or diagnostic purpose. While several examples are herein described with regard to treating bones, other examples can be used in other interior body regions as well. In addition, it is also anticipated that certain examples could be used for purposes other than medical, such as construction, manufacturing, and excavation, among others; accordingly, nothing herein is intended to limit application of the various examples to purely medical uses.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention, as defined by the following claims.

What is claimed is:

1. A surgical saw apparatus comprising:
a holding member including an outer surface and an elongated slot open at a first end, wherein the elongated slot includes spaced apart elongated sides, a holding surface extending between the elongated sides, and an end surface at a second end, opposite the first end of the elongated slot;
a clamping member having a clamping surface disposed adjacent the elongated slot and movable within the elongated slot;
a releasing pin having a first end, rigidly attached to the clamping member and slidably attached to the holding member, a second end disposed away from the clamping member and the holding member, and an axis extending between the first and second ends;
a housing; and
a sleeve holding the releasing pin to slide parallel to the axis of the releasing pin, wherein the sleeve is mounted within the housing to rotate about the axis of the releasing pin,
wherein moving the releasing pin relative to the holding member, in a releasing direction, parallel to the axis of the releasing pin, moves the clamping surface away from the holding surface.

2. The apparatus of claim 1, wherein
the apparatus additionally includes a cross pin, rigidly attached to the first end of the releasing pin to extend perpendicular to the axis of the releasing pin,
the clamping member additionally includes a round hole,
the cross pin extends through the round hole to attach the clamping member to the releasing pin,
the holding member additionally includes a slotted hole, slotted in a direction parallel to the axis of the releasing pin, and
the cross pin extends through the slotted hole to slidably attach the holding member to the releasing pin.

3. The apparatus of claim 1, wherein
the releasing pin additionally includes an outwardly-extending flange facing opposite the releasing direction,
the second end of the releasing pin extends beyond the sleeve;

the sleeve additionally includes an inwardly-extending flange facing in the releasing direction, and the apparatus additionally comprises a compression spring extending between the outwardly-extending flange of the releasing pin and the inward-extending flange of the sleeve.

4. A surgical saw apparatus comprising:

a housing;

a drive plate;

a holding member mounted to rotate about an axis of rotation, wherein the holding member is held within an engaged position to rotate with the drive plate, and wherein the holding member is additionally movable into a released position to rotate independently from the drive plate;

a clamping member mounted to rotate with the holding member about the axis of rotation, wherein the clamping member is held on the holding member in a clamping position, wherein the clamping member is movable away from the holding member into an open position, wherein the holding member and the clamping member in the clamping position form an elongated slot, having an open end, for holding a shank of a surgical saw blade having a blade portion extending outward from the open end of the elongated slot, and wherein the holding member and the clamping member in the clamping position form an elongated slot for releasing the shank of a surgical saw blade for removal through the open end of the elongated slot; and a releasing pin holding the holding member in the engaged position while additionally holding the clamping member in the clamping position, wherein the releasing pin is movable into a released position, wherein the releasing pin in the released position holds the holding member in the released position and the clamping member in the open position.

5. The surgical saw apparatus of claim 4, additionally comprising:

a motor;

a drive shaft, rotationally driven by the motor;

an eccentric shaft disposed at an end of the drive shaft; and a roller, rotatably mounted on the eccentric shaft, wherein the drive plate additionally includes spaced-apart contact surfaces engaging opposite sides of the roller to drive the drive plate in oscillating rotation.

6. The surgical saw apparatus of claim 4, wherein the apparatus additionally comprises a handle portion extending outwardly from the axis of rotation in a direction perpendicular to the axis of rotation, and the holding member can be engaged with the drive plate at a plurality of different angles about the axis of rotation, whereby the holding member can be caused to be driven in oscillating rotation through a plurality of different angles about the axis of rotation relative to the handle portion.

7. The surgical saw apparatus of claim 6, wherein the drive plate includes a plurality of grooves, disposed in a circular pattern about the axis of rotation, and the holding member includes a plurality of teeth, disposed in a circular pattern about the axis of rotation, held within the grooves with the holding member in the engaged position, and moved away from the grooves with the holding member in the released position.

8. The surgical saw apparatus of claim 6, wherein the drive plate includes a central hole having an inward-extending flange, facing opposite a releasing direction, the releasing pin extends through the central hole of the drive plate from a first end of the releasing pin, operatively connected to the holding member and to the clamping member, to a second end, outwardly disposed from the drive plate and from the housing, the releasing pin includes an outward-extending flange, facing in the releasing direction, and the releasing pin is moved into the released position by moving the second end of the releasing pin the releasing direction.

9. The surgical saw apparatus of claim 8, wherein the apparatus additionally includes a cross pin, rigidly attached to the first end of the releasing pin to extend perpendicular to an axis of the releasing pin, the clamping member additionally includes a round hole, the cross pin extends through the round hole to attach the clamping member to the releasing pin, the holding member additionally includes a slotted hole, slotted in a direction parallel to the axis of the releasing pin, and the cross pin extends through the slotted hole to slidably attach the holding member to the releasing pin.

10. The surgical saw apparatus of claim 6, wherein the elongated slot open at one end is formed by a slot within the holding member, and the clamping member includes a clamping surface held within the slot within the holding member with the clamping member in the clamping position.

11. A surgical saw apparatus comprising.

a surgical saw blade;

a housing;

a drive plate, mounted in the housing to rotate about an axis of rotation, driven in oscillating rotation, having a groove radially displaced from the axis of rotation and a central hole coaxial with the axis of rotation having an inward-extending flange facing opposite a releasing direction;

a holding member, releasably holding the surgical saw blade and including a tooth extending toward the drive plate, where the holding member is mounted in the housing to rotate about the axis of rotation, to slide along the axis of rotation in the releasing direction from an engaged position, in which the tooth is held within the groove to a released position, in which the tooth is held away from the groove, and opposite the releasing direction;

a releasing pin, extending along the axis of rotation between a first end, operatively connected to the holding member, and a second end extending outward from the drive plate and from the housing, the releasing pin including an outward-extending flange facing the releasing direction; and a compression spring, extending around the releasing pin between an inward-extending flange of the drive plate and the outward-extending flange of the releasing pin.

12. The surgical saw apparatus of claim 11, wherein the drive plate additionally includes a plurality of grooves arranged in a first circular pattern, the holding member additionally includes a plurality of teeth arranged in a second circular pattern, the drive plate and the holding member are brought together at a plurality of different angles relative to one another about the axis of rotation, with the holding member in the engaged position, and all of the teeth and grooves are spaced apart from one another with the holding member in the released position.

13. The surgical saw apparatus of claim 12,
wherein the first end of the releasing pin is operatively connected to the holding member to move the holding member in the releasing direction and opposite the releasing direction and the second end of the releasing pin extends through the central hole within the drive plate,
wherein the compression spring applies a force holding the holding member in engagement with the drive plate to the outward-extending flange of the releasing pin,
wherein the holding member is moved into the released position by pushing the second end of the releasing pin in the releasing direction.

14. The surgical saw apparatus of claim 13, wherein
the holding member additionally includes an elongated slot, open at a first end and including spaced apart elongated sides, a holding surface, extending between the elongated sides, and an end surface at a second end, opposite the first end of the slot,
the apparatus additionally includes a clamping member having a clamping surface disposed adjacent the elongated slot and movable within the elongated slot,
the first end of the of the releasing pin is operatively connected to the clamping member,
the compression spring applies a force pulling the clamping surface toward the holding surface to the outward-extending flange of the releasing pin, and
the clamping surface is moved away from the holding surface by pushing the second end of the releasing pin in the releasing direction.

15. The surgical saw apparatus of claim 14, wherein
the apparatus additionally includes a cross pin, rigidly attached to the first end of the releasing pin to extend perpendicular to an axis of the releasing pin,
the clamping member additionally includes a round hole,
the cross pin extends through the round hole to attach the clamping member to the releasing pin,
the holding member additionally includes a slotted hole, slotted in a direction parallel to the axis of the releasing pin, and
the cross pin extends through the slotted hole to slidably attach the holding member to the releasing pin.

16. The surgical saw apparatus of claim 14, wherein
the surgical saw blade includes an elongated shank at a proximal end of the surgical saw blade, having peripheral surfaces, including parallel elongated straight side surfaces and a proximal end surface, fitting within the elongated slot of the holding member,
the elongated shank of the surgical saw blade is held within the elongated slot of the holding member by a force transmitted through the releasing pin from the compression spring to hold the clamping member against the elongated shank of the surgical saw blade,
the surgical saw blade additionally includes a blade portion extending outwardly from the elongated shank to a distal end of the surgical saw blade, wherein the distal end of the saw blade includes a plurality of outwardly facing saw teeth disposed along an arcuate line forming an arc about an arc axis coaxial with the axis of the releasing pin with the elongated shank of the saw blade held within the elongated slot of the holding member, and
the elongated shank of the surgical saw blade is released from the elongated slot of the holding member by pushing the second end of the releasing pin in the releasing direction.

17. The surgical saw apparatus of claim 16, wherein
the elongated shank of the surgical saw blade additionally comprises a first aperture disposed midway between the parallel elongated straight side surfaces of the elongated shank,
the clamping member additionally includes a first lug, disposed midway between the elongated sides of the elongated slot within the holding member, to extend opposite the releasing direction from the clamping surface into the first aperture with the elongated shank of the saw blade held within the elongated slot of the holding member,
the first lug is held within the first aperture by force transmitted through the releasing pin from the compression spring to hold the clamping member against the elongated shank of the surgical saw blade, and
the first lug is removed from the first aperture by pushing the end of the releasing pin in the releasing direction.

18. The surgical saw apparatus of claim 17, wherein the first lug includes a locating surface, facing the end surface of the slot, extending perpendicular to the clamping surface, and a slanted surface extending at an oblique angle from the clamping surface to an edge of the locating surface.

19. The surgical saw apparatus of claim 17, wherein
the elongated shank of the surgical saw blade additionally comprises a second aperture, spaced apart from the first aperture and disposed midway between the parallel elongated straight side surfaces of the elongated shank,
the clamping member additionally includes a second lug, disposed midway between the elongated sides of the elongated slot within the holding member, to extend opposite the releasing direction from the clamping surface into the second aperture with the elongated shank of the saw blade held within the elongated slot of the holding member,
the second lug is held within the second aperture by force transmitted through the releasing pin from the compression spring to hold the clamping member against the elongated shank of the surgical saw blade, and
the second lug is removed from the second aperture by pushing the end of the releasing pin in the releasing direction.

20. The surgical saw apparatus of claim 19, wherein the first and second lugs each include a locating surface, facing the end surface of the slot, extending perpendicular to the clamping surface, and a slanted surface extending at an oblique angle from the clamping surface to an edge of the locating surface.

* * * * *